(12) United States Patent
Suorsa et al.

(10) Patent No.: US 6,344,037 B1
(45) Date of Patent: Feb. 5, 2002

(54) INTEGRATED COAXIAL TRANSMISSION LINE AND FLEXIBLE DRIVE CABLE

(75) Inventors: Veijo T. Suorsa, Sunnyvale; Don S. Mamayek, Mountain View, both of CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/017,578

(22) Filed: Feb. 3, 1998

(51) Int. Cl.$^7$ ............................................. A61M 25/01
(52) U.S. Cl. ..................... 604/528; 604/22; 604/264; 600/433; 600/437
(58) Field of Search .............. 604/22, 264, 523, 604/538, 526–28, 533–34; 606/159, 161, 168–171; 336/82, 83, 84, 100, 117–20; 600/462, 463, 433–35, 437, 459

(56) References Cited

U.S. PATENT DOCUMENTS

| | | | |
|---|---|---|---|
| 3,938,502 A | 2/1976 | Bom | 128/2 |
| 4,155,259 A | 5/1979 | Engeler | 73/626 |
| 4,576,177 A | 3/1986 | Webster, Jr. | 128/660 |
| 4,771,774 A | 9/1988 | Simpson et al. | 128/305 |
| 4,794,931 A * | 1/1989 | Yock | 128/660.03 |
| 5,095,911 A | 3/1992 | Pomeranz | 128/662.06 |
| 5,108,411 A | 4/1992 | McKenzie | 606/159 |
| 5,156,154 A | 10/1992 | Valenta, Jr. et al. | 128/661.09 |
| 5,188,106 A | 2/1993 | Nappholz et al. | 128/419 |
| 5,203,338 A | 4/1993 | Jang | 128/662.06 |
| 5,217,456 A | 6/1993 | Narciso, Jr. | 606/15 |
| 5,248,296 A * | 9/1993 | Alliger | 609/22 |
| 5,347,256 A | 9/1994 | Yumiki et al. | 336/84 |
| 5,348,017 A | 9/1994 | Thornton et al. | 128/662.06 |
| 5,359,312 A | 10/1994 | Choi | 336/84 |
| 5,406,951 A | 4/1995 | ten Hoff et al. | 128/662.06 |
| 5,429,136 A | 7/1995 | Milo et al. | 128/660.03 |
| 5,437,282 A | 8/1995 | Koger et al. | 128/662.06 |
| 5,503,154 A * | 4/1996 | Belef | 128/662.03 |
| 5,503,155 A | 4/1996 | Salmon et al. | 128/662.06 |
| 5,549,108 A | 8/1996 | Edwards et al. | 128/642 |
| 5,558,092 A | 9/1996 | Unger et al. | 128/660.03 |
| 5,590,653 A | 1/1997 | Aida et al. | 128/653.2 |

(List continued on next page.)

FOREIGN PATENT DOCUMENTS

| | | |
|---|---|---|
| EP | 0 234 951 | 2/1987 |
| FR | 2 569 341 | 8/1984 |
| WO | WO 92/16147 | 3/1992 |

OTHER PUBLICATIONS

Roy W. Martin et al., "Design Characteristics for intravascular ultrasonic catheters," *International Journal of Cardiac Imaging 4*, pp. 201–216, 1989.

M. Arditi et al., "An Annular Array System for High Resolution Breast Echography," *Ultrasonic Imaging 4*, pp. 1–31, 1982.

R.B. Bernardi et al., "A Dynamically Focused Annular Array,"0 1976 Ultrasonics Symposium Proceedings, IEEE Cat. #76 CH1120–5SU, pp. 157–159.

*Primary Examiner*—Angela D. Sykes
*Assistant Examiner*—Patricia Bianco
(74) *Attorney, Agent, or Firm*—Townsend and Townsend and Crew, LLP

(57) ABSTRACT

The present invention provides for integrated coaxial drive cables and transmission lines for use in catheter systems. In one embodiment, the invention comprises a catheter system comprising a catheter body having a distal end, a proximal end and a working lumen. A drive cable extends through the catheter body's working lumen and comprises an outerwound layer, an innerwound layer and a central lumen. A coaxial cable is provided comprising a conducting core and an insulation layer. The coaxial cable is disposed to extend through and fill the central lumen.

21 Claims, 3 Drawing Sheets

U.S. PATENT DOCUMENTS

| | | | |
|---|---|---|---|
| 5,598,845 A | 2/1997 | Chandraratna et al. | 128/662.03 |
| 5,620,417 A | 4/1997 | Jang et al. | 604/96 |
| 5,816,923 A * | 10/1998 | Milo et al. | 464/58 |
| 6,078,831 A * | 10/1998 | Belef et al. | 600/424 |
| 5,868,767 A * | 2/1999 | Farley et al. | 606/159 |
| 5,938,609 A * | 8/1999 | Pomeranz | 600/439 |
| 5,967,978 A * | 10/1999 | Littmann et al. | 600/381 |
| 6,004,269 A * | 12/1999 | Crowley et al. | |
| 6,027,460 A * | 2/2000 | Shturman et al. | 600/585 |

* cited by examiner

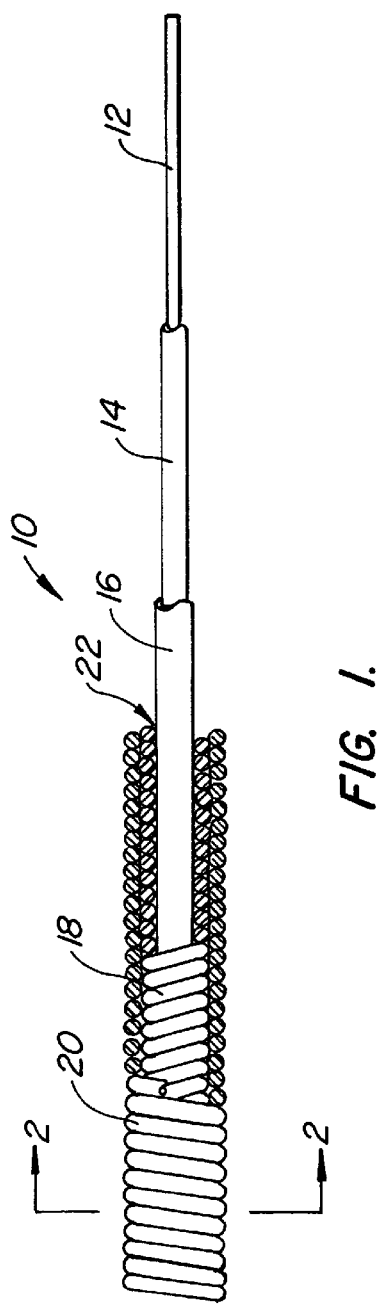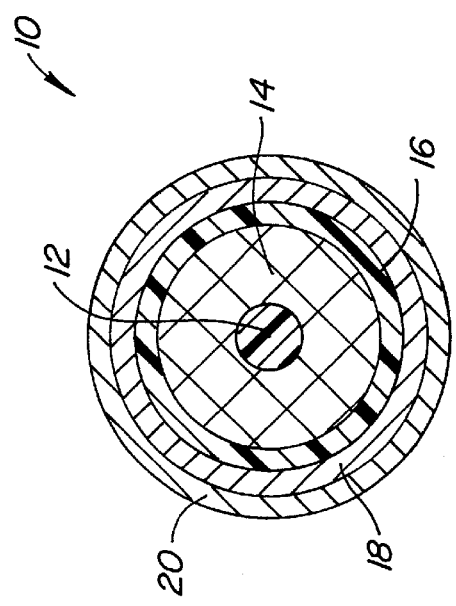

INTEGRATED COAXIAL TRANSMISSION LINE AND FLEXIBLE DRIVE CABLE

BACKGROUND OF THE INVENTION

The present invention relates generally to the construction of flexible, torque-transmitting devices, and more particularly to the construction of drive cables for rotation of ultrasonic transducers for use in vascular catheters.

Intravascular imaging of blood vessel lesions prior to percutaneous transluminal angioplasty, atherectomy, and other interventional procedures, promises to be of great benefit. A particularly successful design for an intravascular imaging catheter employs a rotatable ultrasonic transducer, where the transducer is attached to the distal end of a flexible drive cable. The transducer may be rotated within a catheter body or sheath in order to transmit an ultrasonic signal and produce a video image by well-known techniques.

Although very successful, the need to reduce the size of the drive cable to very small diameters (to be compatible with introduction into very small coronary arteries) presents a number of technical challenges. In addition to the very small diameter, the drive cable should be highly flexible so that it can pass through the tortuous regions of the vasculature, particularly the coronary arteries. It is also very important that the drive cable provides uniform rotation along its entire length, i.e., avoid rotational wind-up which can cause variations in the rotational speed of the transducer and result in image distortions.

The construction of transducer drive cables for intravascular ultrasound devices is further complicated by the desire to run transducer lead wires or transmission lines through a lumen in the cable itself. Such designs attempt to avoid an increase in an effective diameter which may result from placing the leads on the surface of the drive cable. Coaxial lead cables have been utilized in the past and have the added advantage that they provide radio frequency (RF) noise shielding. Coaxial cables, however, suffer in that they are generally large and difficult to use in the smallest intravascular devices, e.g., coronary devices. Coaxial cables also are typically manufactured separately from the drive cables, which requires that the drive cable lumen be large enough to allow the coaxial cable to be fed through. The resulting gap between the coaxial cable and drive cable further adds to the drive cable's overall outer diameter.

It would be therefore desirable to provide improved drive cables for ultrasonic transducers and other rotatable electrical sensors. It would be particularly desirable to provide drive cables which can be constructed to have small diameters while still incorporating transmission lines. Preferably, the combined drive cable and transmission line will provide uniform torque-transmission along the entire length of the drive cable in order to produce ultrasonic images having a minimum distortion. The drive cables should further provide sufficient RF shielding of the electrical transmission lines.

SUMMARY OF THE INVENTION

The present invention provides for integrated flexible drive cables and coaxial transmission lines for use in catheter systems. In one embodiment, the invention provides a catheter system comprising a catheter body having a distal end, a proximal end and a working lumen. A drive cable extends through the working lumen and comprises an outerwound layer, an innerwound layer and a central lumen. A coaxial cable is provided comprising a conducting core and an insulation layer. The coaxial cable is disposed to extend through and fill the central lumen.

In one aspect of the invention, the innerwound layer comprises a combination of stainless steel wire and at least one material comprising copper, gold, silver, aluminum, magnesium or an alloy made from at least one of these metals. In this manner, the innerwound layer provides exemplary mechanical properties from the stainless steel, and also exemplary shielding properties from the other metal or metal alloy.

In another aspect, the drive cable has an outer diameter between about 0.005 inches and about 0.150 inches. Such a diameter facilitates the use of the drive cable with small catheter bodies. In one aspect, both the innerwound layer and outerwound layer comprise stainless steel wire. In this manner, the drive cable comprises two layers of stainless steel wire.

In another aspect, the innerwound layer comprises a shape memory or superelastic alloy metal wire, such as wire made from nitinol (nickel titanium), nickel titanium copper, nickel titanium aluminum, or the like. In one aspect, the outerwound layer comprises a shape memory or superelastic alloy metal wire.

In one particular aspect, the catheter system further comprises a working element operably attached to the drive cable. In one aspect, the working element is a transducer. Alternatively, the working element is an annular array of transducer elements.

In another particular aspect, the coaxial cable further comprises a shield layer. Such a shield layer facilitates the conduction of electrical signals through the conducting core without experiencing external electrical interference which may adversely affect the signals. In one aspect, the shield layer comprises at least one material selected from a group of materials consisting of silver-plated copper, gold, aluminum, and alloys made from at least one of these metals. Such a selection of metals facilitates the shielding capability of the shield layer.

In another aspect, the drive cable, which includes a coaxial cable containing a shield layer disposed within the drive cable's central lumen, has an outer diameter between about 0.005 inches and about 0.150 inches.

In one preferred embodiment, the invention provides an integrated drive cable and transmission line for a catheter comprising a conducting core having a layer of insulation. The integrated drive cable and transmission line further includes an innerwound layer adjacent to and surrounding the layer of insulation, and an outerwound layer adjacent to and surrounding the innerwound layer.

In one aspect, the innerwound layer comprises a combination of stainless steel wire and at least one material selected from a group of materials consisting of copper, gold, silver, aluminum, magnesium, copper alloy, gold alloy, silver alloy, aluminum alloy and magnesium alloy. Such an innerwound composition facilitates the shielding of external electrical interference as well as providing a drive cable of sufficient flexibility and strength. In another aspect, the outerwound layer has an outer diameter between about 0.005 inches and about 0.150 inches.

In one particular aspect, the innerwound layer comprises stainless steel wire to assist in providing uniform rotation over the length of the cable. In another aspect, the outerwound layer also comprises stainless steel wire.

In still another preferred embodiment, the invention provides an integrated drive cable and transmission line for a catheter comprising a conducting core having a layer of insulation, and a shield layer adjacent to and surrounding the layer of insulation. The drive cable and transmission line further comprises an innerwound layer adjacent to and surrounding the shield layer. An outerwound layer is provided adjacent to and surrounding the innerwound layer.

In one aspect, the shield layer comprises at least one of silver-plated copper, gold, aluminum, silver-plated copper alloy, gold alloy and aluminum alloy. In another aspect, the outerwound layer has an outer diameter between about 0.005 inches and about 0.150 inches. In a further aspect, the innerwound and outerwound layers comprise stainless steel wire.

In one aspect, the innerwound layer comprises a shape memory or superelastic alloy metal wire, such as wire made from nitinol (nickel titanium), nickel titanium copper, nickel titanium aluminum, or the like. In another aspect, the outerwound layer comprises wire made from a shape memory or superelastic alloy metal.

BRIEF DESCRIPTION OF THE DRAWINGS

FIG. 1 is a partially cut-away side view of an integrated flexible drive cable and coaxial transmission line according to the present invention.

FIG. 2 is a cross-sectional view of the integrated drive cable and transmission line depicted in FIG. 1 taken along line 2—2.

DESCRIPTION OF THE PREFERRED EMBODIMENT

Figure 3:
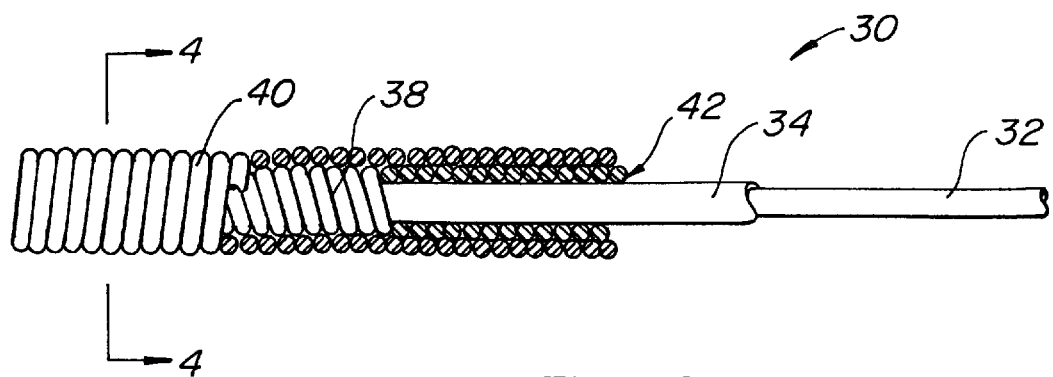
FIG. 3 is a partially cut-away side view of an alternative embodiment of an integrated drive cable and coaxial transmission line according to the present invention.

The present invention provides exemplary integrated flexible drive cables and coaxial transmission lines for use in catheter systems. In particular, the present invention integrates a flexible drive cable and a coaxial transmission line running through a central lumen of the drive cable. The integrated combination provides a smaller outer diameter than typical coaxial cable/drive cable combinations by eliminating one or more layers. For example, a typical coaxial cable includes an outer jacket layer which holds the inner layers in place. The present invention eliminates the use of such a jacket and instead uses the inner surface of the drive cable to hold the coaxial cable inner layers in place. Further, a typical coaxial cable and drive cable combination has a gap separating the two components. Such a gap is necessary to allow the coaxial cable to be fed into the central lumen of the drive cable. The present invention eliminates such a gap by forming the drive cable around the coaxial cable.

By eliminating layers in a coaxial cable and drive cable combination, the overall outer diameter of the integrated combination is smaller. Such a smaller diameter facilitates the use of the integrated drive cable and coaxial cable in smaller catheters and, therefore, in smaller vasculatures.

Turning now to FIGS. 1 and 2, an integrated coaxial transmission line and flexible drive cable body 10 will be described. As shown, integrated cable body 10 comprises several layers extending the length of the cable body 10. First, a conducting core 12 is provided. An insulation layer 14 is adjacent to and surrounds the core 12. The insulation layer 14 is preferably made from fluoropolymers such as FEP, PFA, and the like. A shield layer 16 is adjacent to and surrounds the insulation layer 14. The shield layer preferably comprises silver-plated copper, gold, aluminum, silver-plated copper alloys, gold alloys, aluminum alloys, or the like.

An innerwound layer 18 is adjacent to and surrounds the shield layer 16. The innerwound layer 18 preferably comprises 304 V stainless steel wire. The innerwound layer 18 may also comprise a combination of stainless steel and at least one material selected from a group of materials comprising copper, gold, silver, aluminum, magnesium, copper alloy, gold alloy, silver alloy, aluminum alloy, magnesium alloy, or the like. An outerwound layer 20, preferably made from 304 V stainless steel, is adjacent to and surrounds the innerwound layer 18. Innerwound layer 18 and outerwound layer 20 may also be made from a shape memory or superelastic alloy metal wire, such as wire made from nitinol (Ni/Ti), Ni/Ti/Cu, Ni/Ti/Al, or the like.

The physical characteristics of preferable innerwound and outerwound layers are disclosed in U.S. Pat. Nos. 5,503,155; 5,208,411; and "Design Characteristics of Intravascular Ultrasonic Catheters" by Roy W. Martin and Christopher C. Johnson, the disclosures of which are hereby incorporated by reference.

In the present invention, innerwound layer 18 and outerwound layer 20 are counterwound to enable one of the layers 18, 20 to constrict when the integrated cable body 10 is rotated. For example, clockwise rotation of the integrated cable body 10 may cause the innerwound layer 18 to constrict. Counter-clockwise rotation of the integrated cable body 10 will then cause the outerwound layer 20 to constrict. In this manner, rotation of the integrated cable body 10, will result in the core 12, insulation 14, and shield 16 remaining held together by the constricting innerwound 18 or outerwound 20 layer. Preferably, rotation of integrated cable body 10 causes outerwound layer 20 to constrict.

The outerwound layer 20 and innerwound layer 18 create a central lumen 22, into which the core 12, insulation layer 14 and shield layer 16 are integrally disposed. This can be accomplished by forming the drive cable over the coaxial transmission line.

The integrated transmission line and flexible drive cable can be manufactured using the same techniques as used for the manufacture of miniature coaxial cables. Insulation layer 14 is extruded onto the outer surface of core 12. Shield layer 16 is then served onto the outer surface of insulation layer 14. Next, innerwound layer 18 is served onto the top of shield layer 16. Outerwound layer 20 is served onto the top of innerwound layer 18. This method of manufacture helps eliminate the gap between the transmission line and the flexible drive cable.

The arrangement of integrated cable body 10 differs from typical drive cable and coaxial cable combinations where the drive cables are not integrally formed around the coaxial cables. In such a case, the central lumen must be large enough to allow the coaxial cable to be fed through the lumen. After feeding the coaxial cable into the lumen, a gap remains between the outer surface of the coaxial cable and the inner surface of the innerwound layer. This clearance is needed to allow the two cables to be manufactured separately and fit together. Such a scenario adds to the overall outer diameter of the drive cable. In the present invention, however, the gap between the innerwound and the coaxial transmission line is eliminated.

Figure 4:
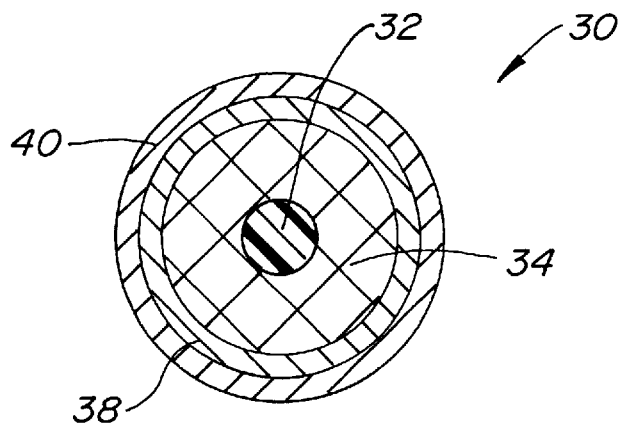
FIG. 4 is a cross-sectional view of the integrated drive cable and transmission line depicted in FIG. 3 taken along line 4—4.

Turning now to FIGS. 3 and 4, an alternative integrated coaxial transmission line and flexible drive cable body 30 according to the present invention will be described. Integrated cable body 30 comprises a conducting core 32, surrounded by an adjacent insulation layer 34. An innerwound layer 38 and an outerwound layer 40 are counterwound around the insulation layer 34. In other words, the two layers are wound such that rotation of the integrated cable body 30 will cause one of the layers to constrict (preferably outerwound layer 40) and the other to expand (preferably innerwound layer 38). In this way, the innerwound layer 38 and outerwound layer 40 cooperate during rotation of integrated cable body 30 to hold together the core 32 and insulation layer 34 contained within the innerwound layer 38.

A central lumen 42 exists inside innerwound layer 38 which is filled by the conducting core 32 and insulation layer 34. As previously noted, such an arrangement is unlike typical coaxial cable and drive cable combinations which require a central lumen large enough to accommodate a separately manufactured coaxial cable.

The method of manufacture of integrated cable body 30 is similar to that of integrated cable body 10, but without the need to use a shield layer. Insulation layer 34 is extruded onto the outer surface of core 32. Next, innerwound layer 38 is served onto the top of the outer surface of insulation layer 34. Outerwound layer 40 is served onto the top of innerwound layer 38. This method of manufacture helps eliminate the gap between the two components.

Further, the integrated flexible drive cable and coaxial transmission line of FIG. 3 has a smaller outer diameter than typical drive cable and coaxial cable combinations. This is accomplished by eliminating the gap between the drive cable inner surface and the coaxial cable outer surface, and by eliminating a typical coaxial cable jacket often used to hold the coaxial cable's inner layers in place. In other words, the coaxial cable layers (core 32 and insulation layer 34 in FIG. 4) fill the central lumen within the integrated cable body 30.

In the preferred embodiment depicted in FIGS. 3 and 4, the shield layer is eliminated, and the innerwound layer 38 is constructed to have shielding qualities, thereby further reducing the outer diameter of the drive cable and coaxial cable combination. Such an innerwound layer 38 is preferably made of materials that provide mechanical properties and electrical properties similar to those for separate shield and innerwound layers. Such materials comprise a combination of stainless steel and copper, stainless steel and silver, and the like. Even though this embodiment eliminates the shield layer, it still provides exemplary shielding qualities by incorporating material having shielding characteristics into the innerwound layer 38.

Figure 5:
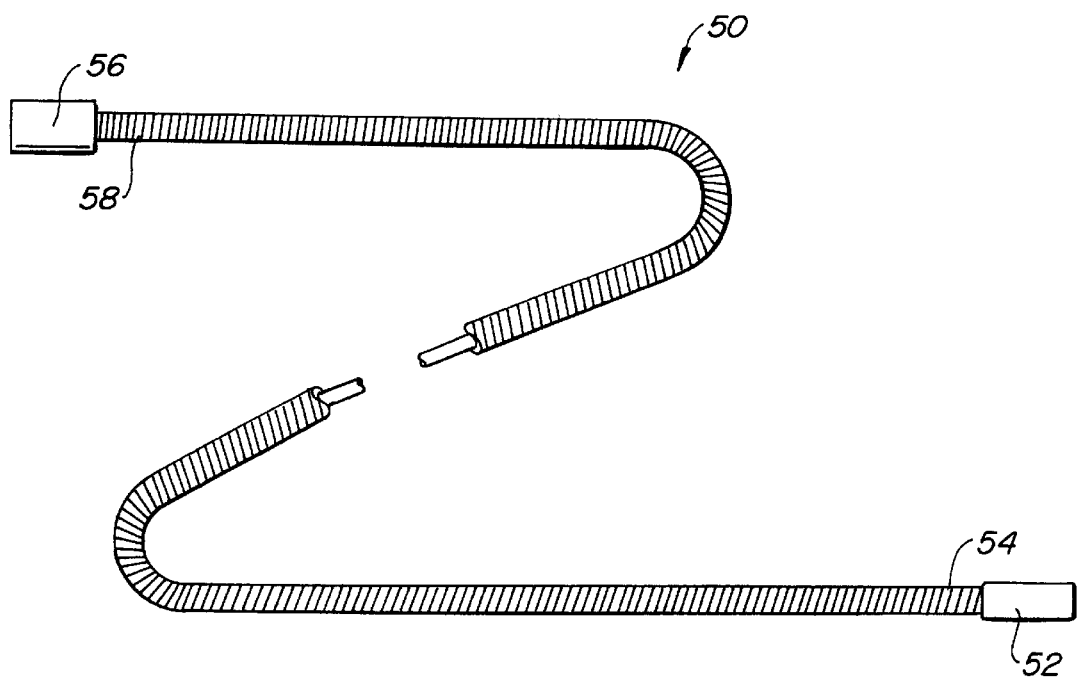
FIG. 5 illustrates the integrated flexible drive cable and coaxial transmission line of FIG. 1 shown with a working element and a coupling element connected to its ends.

FIG. 5 depicts a flexible drive cable 50 having a distal end 54 and a proximal end 58. A working element 52 is operably attached to the distal end 54. The working element, which may comprise a single element transducer, an annular array of transducer elements, or the like, is also operably attached to the conducting core. In this way, electrical signals can be transmitted to or from the working element. For example the present invention may use a working element such as the annular array disclosed in co-pending U.S. patent application Ser. No. 09/017,581, filed contemporaneously herewith, the disclosure of which is hereby incorporated by reference.

A coupling element 56 is operably attached to the proximal end 58 of drive cable 50. The coupling element 56 is used to couple the drive cable 50 to image processing 35 equipment and/or a controller (not shown), which would operate to control the catheter. For example, such a coupling element 56 could be coupled to a rotary transformer, such as that disclosed in co-pending U.S. patent application Ser. No. 09/017,583, now U.S. Pat. No. 6,017,312, issued Jan. 25, 2000, filed contemporaneously herewith, the disclosure of which is hereby incorporated by reference.

Figure 6:
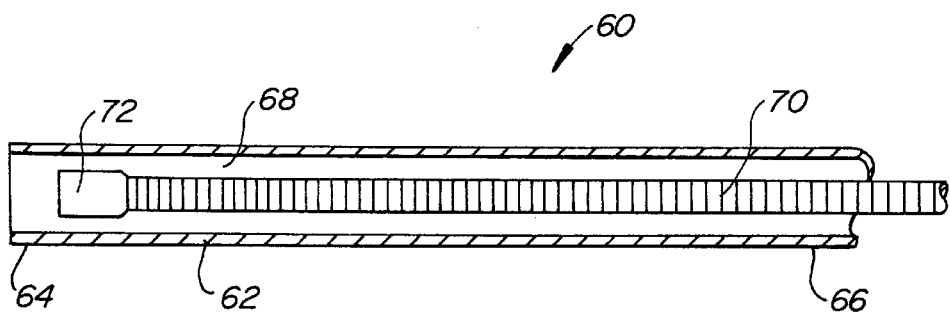
FIG. 6 is a cross-sectional view of a catheter system having an integrated flexible drive cable and coaxial transmission line according to the present invention.

Turning now to FIG. 6, a catheter system 60 according to the present invention will be described. Catheter system 60 comprises a catheter body 62 having a distal end 64, a proximal end 66, and a working lumen 68. A flexible drive cable 70, such as the cable bodies described in conjunction with FIGS. 1 and 2, or FIGS. 3 and 4, is also provided. A working element 72 is operably attached to the flexible drive cable 70. By using a coaxial cable for the transmission line, exemplary RF shielding is provided for the electrical signals carried by the coaxial cable.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A catheter system comprising;
   a catheter body having a distal end, a proximal end and a working lumen;
   a drive cable extending through said working lumen, the drive cable comprising an outerwound layer, an innerwound layer and a central lumen; and
   a coaxial cable extending through said central lumen, the coaxial cable consisting essentially of a conducting core and an insulation layer overlying said core, wherein said coaxial cable is disposed within and substantially fills said central lumen so that at least a portion of said insulation layer contacts said innerwound layer;
   wherein the innerwound layer comprises a combination of stainless steel wire and at least one of the following: copper, gold, silver, aluminum, magnesium.

2. A catheter system as in claim 1, herein the drive cable has an outer diameter between about 0.005 inches and about 0.150 inches.

3. A catheter system as in claim 1, wherein the outerwound layer comprises stainless steel wire.

4. A catheter system as in claim 1 wherein the outerwound layer comprises a shape memory or superelastic alloy metal wire.

5. A catheter system as in claim 4, wherein the shape memory or superelastic alloy metal wire comprises nitinol.

6. A catheter system as in claim 1, further comprising a working element operably attached to said drive cable.

7. A catheter system as in claim 6, wherein the working element comprises a transducer.

8. A catheter system comprising;
   a catheter body having a distal end, a proximal end and a working lumen;
   a drive cable extending through said working lumen, the drive cable comprising an outerwound layer, an innerwound layer and a central lumen; and
   a coaxial cable extending through said central lumen, the coaxial cable consisting essentially of a conducting core and an insulation layer overlying said core, wherein said coaxial cable is disposed within and substantially fills said central lumen so that at least a portion of said insulation layer contacts said innerwound layer;

wherein the innerwound layer comprises a combination of stainless steel wire and an alloy made from at least one of the following:
   copper, gold, silver, aluminum, magnesium.

9. A catheter system as in claim 8, wherein the drive cable has an outer diameter between about 0.005 inches and about 0.150 inches.

10. A catheter system comprising:
   a catheter body having a distal end, a proximal end and a working lumen;
   a drive cable extending through said working lumen, the drive cable comprising an outerwound layer, an innerwound layer and a central lumen; and
   a coaxial cable extending through said central lumen, the coaxial cable consisting essentially of a conducting core and an insulation layer, wherein said coaxial cable is disposed within and substantially fills said central lumen so that at least a portion of said insulation layer contacts said innerwound layer;
   wherein the innerwound layer comprises a shape memory or superelastic alloy metal wire.

11. A catheter system as in claim 10, wherein the shape memory or superelastic alloy metal wire comprises nitinol.

12. A catheter system as in claim 10 wherein the outerwound layer comprises a shape memory or superelastic alloy metal wire.

13. A catheter system comprising:
   a catheter body having a distal end, a proximal end and a working lumen;
   a drive cable extending through said working lumen, the drive cable comprising an outerwound layer, an innerwound layer and a central lumen;
   a coaxial cable extending through said central lumen, the coaxial cable comprising a conducting core and an insulation layer, wherein said coaxial cable is disposed within and substantially fills said central lumen; and
   a working element operably attached to said drive cable, wherein the working element comprises an annular array of transducer elements.

14. A catheter system comprising;
   a catheter body having a distal end, a proximal end and a working lumen;
   a drive cable extending through said working lumen, the drive cable comprising an outerwound layer, an innerwound layer and a central lumen; and
   a coaxial cable extending through said central lumen, wherein said coaxial cable is disposed within and substantially fills said central lumen;
   wherein the coaxial cable consists essentially of a conducting core, an insulation layer overlying said core and a shield layer overlying said insulation layer; and
   wherein at least a portion of said shield layer contacts said innerwound layer.

15. A catheter system as in claim 14, wherein the shield layer comprises at least one of the following:
   silver-plated copper, gold, aluminum.

16. A catheter system as in claim 14, wherein the shield layer comprises an alloy made from at least one of the following:
   silver-plated copper, gold, aluminum.

17. A catheter system comprising;
   a catheter body having a distal end, a proximal end and a working lumen;
   a drive cable extending through said working lumen, the drive cable comprising an outerwound layer, an innerwound layer and a central lumen; and
   a coaxial cable extending through said central lumen, the coaxial cable consisting essentially of a conducting core and an insulation layer, wherein said coaxial cable is disposed within and substantially fills said central lumen so that at least a portion of said insulation layer contacts said innerwound layer;
   wherein the coaxial cable consists essentially of a conducting core, an insulation layer and a shield layer, wherein at least a portion of said shield layer contacts said innerwound layer; and
   wherein the drive cable has an outer diameter between about 0.005 inches and about 0.150 inches.

18. A catheter system comprising:
   a catheter body having a distal end, a proximal end and a working lumen;
   a drive cable extending through said working lumen, the drive cable comprising an outerwound layer, an innerwound layer and a central lumen; and
   a jacket-less coaxial cable extending through said central lumen, the coaxial cable comprising a conducting core and an insulation layer, wherein said coaxial cable is disposed within and substantially fills said central lumen so that at least a portion of said insulation layer contacts said innerwound layer;
   wherein said jacket-less coaxial cable further comprises a shield layer over said insulation layer, wherein at least a portion of said shield layer contacts said innerwound layer instead of said portion of said insulation layer.

19. A catheter system comprising:
   a catheter body having a distal end, a proximal end and a working lumen;
   a drive cable extending through said working lumen, the drive cable comprising an outerwound layer, an innerwound layer and a central lumen; and
   a jacket-less coaxial cable extending through said central lumen, the coaxial cable comprising a conducting core and an insulation layer, wherein said coaxial cable is disposed within and substantially fills said central lumen so that at least a portion of said insulation layer contacts said innerwound layer;
   wherein the innerwound layer comprises a combination of stainless steel wire and an alloy made from at least one of the following:
   copper, gold, silver, aluminum, magnesium.

20. A catheter system as in claim 19 wherein the outerwound layer comprises a shape memory or superelastic alloy metal wire.

21. A catheter system comprising:
   a catheter body having a distal end, a proximal end and a working lumen;
   a drive cable extending through said working lumen, the drive cable comprising an outerwound layer, an innerwound layer and a central lumen; and
   a jacket-less coaxial cable extending through said central lumen, the coaxial cable comprising a conducting core and an insulation layer overlying said core, wherein said coaxial cable is disposed within and substantially fills said central lumen so that at least a portion of said insulation layer contacts said innerwound layer;
   wherein the innerwound layer comprises a combination of stainless steel wire and an alloy made from at least one of the following:
   gold, silver, magnesium.

* * * * *